US010488502B2

(12) United States Patent
Bruestle et al.

(10) Patent No.: US 10,488,502 B2
(45) Date of Patent: Nov. 26, 2019

(54) ULTRASOUND PROBE WITH THIN FILM FLEX CIRCUIT AND METHODS OF PROVIDING SAME

(71) Applicant: General Electric Company, Schenectady, NY (US)

(72) Inventors: Reinhold Bruestle, Zipf (AT); Thomas Rittenschober, Zipf (AT); Manuel Schoenauer, Zipf (AT); Andreas Kremsl, Zipf (AT); Rainer Schröder, Bremen (DE)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 364 days.

(21) Appl. No.: 15/497,351

(22) Filed: Apr. 26, 2017

(65) Prior Publication Data

US 2018/0313943 A1    Nov. 1, 2018

(51) Int. Cl.
| | | |
|---|---|---|
| *G01S 7/52* | (2006.01) | |
| *G01S 15/89* | (2006.01) | |
| *G01N 29/24* | (2006.01) | |
| *B06B 1/06* | (2006.01) | |

(52) U.S. Cl.
CPC ............ *G01S 7/5208* (2013.01); *B06B 1/064* (2013.01); *G01N 29/2437* (2013.01); *G01S 15/8925* (2013.01)

(58) Field of Classification Search
CPC ..... G01S 7/5208; G01S 15/8925; B06B 1/02; B06B 1/064; B06B 1/0629; G01N 29/2437
See application file for complete search history.

(56) References Cited

U.S. PATENT DOCUMENTS

| | | |
|---|---|---|
| 5,524,339 A | 6/1996 | Gorowitz |
| 7,527,592 B2 | 5/2009 | Haugen et al. |
| 7,791,252 B2 | 9/2010 | Baumgartner et al. |

(Continued)

FOREIGN PATENT DOCUMENTS

| | | | | |
|---|---|---|---|---|
| WO | WO-2015077593 A1 | * | 5/2015 | ............... H04R 1/40 |
| WO | WO-2018200304 A1 | * | 11/2018 | ........... G01S 7/5208 |

OTHER PUBLICATIONS

International Search Report for related application PCT/US2018/028334, dated Jul. 13, 2018, 4 pages.

(Continued)

*Primary Examiner* — Daniel Pihulic
(74) *Attorney, Agent, or Firm* — Dean D. Small; The Small Patent Law Group, LLC

(57) ABSTRACT

An ultrasound probe and method of forming an ultrasound probe are provided. The ultrasound probe comprises a two-dimensional (2D) transducer assembly having transducer elements arranged in rows and columns. The transducer elements have front and rear surfaces. The front surface is configured to transmit and receive ultrasound signals to and from an object of interest. A thin film flex circuit extends along the rear surface of the transducer assembly. The flex circuit has conductive traces arranged in layers and enclosed within a common dielectric layer. The dielectric layer has a homogeneous composition surrounding the layers of the conductive traces. The conductive traces are electrically interconnected to the corresponding transducer elements.

20 Claims, 9 Drawing Sheets

(56) References Cited

U.S. PATENT DOCUMENTS

| | | |
|---|---|---|
| 7,952,260 B2 | 5/2011 | Haider et al. |
| 9,017,262 B2 | 4/2015 | Bruestle et al. |
| 9,072,487 B2 | 7/2015 | Hebrard et al. |
| 9,539,667 B2 | 1/2017 | Bruestle et al. |
| 2008/0116552 A1 | 5/2008 | Rose et al. |
| 2013/0085394 A1* | 4/2013 | Corbett, III .............. A61B 8/12 600/462 |
| 2016/0295319 A1* | 10/2016 | Douglas ................... H04R 1/40 |
| 2018/0313943 A1* | 11/2018 | Bruestle ................ G01S 7/5208 |

OTHER PUBLICATIONS

Written Opinion for related application PCT/US2018/028334, dated Jul. 13, 2018, 6 pages.

* cited by examiner

ULTRASOUND PROBE WITH THIN FILM FLEX CIRCUIT AND METHODS OF PROVIDING SAME

FIELD

Embodiments described herein generally relate to electronic ultrasound probes and more particularly to electronic assemblies within ultrasound probes.

BACKGROUND OF THE INVENTION

In many ultrasound imaging systems, transducer element signals are generated in a hand-held probe unit and sent to a system console through a multi-channel cable system. In some ultrasound systems, a probe may utilize a relatively large two dimensional (2D) array of 2000 to 20000 transducer elements with each element connected to the console via a separate channel within the cable system. There are applications in which it is desirable for large ultrasound arrays to contain thousands or tens of thousands of transducer elements. As the number of the individual transducer elements increases, the number of separate channels similarly increases.

Today, one or more flexible circuits are connected to the transducer elements to form the individual channels that convey signals to and from corresponding transducer elements. Each flexible circuit includes an array of conductive traces sandwiched between insulating layers, where each conductive trace is connected to a corresponding transducer element. Multiple flexible circuits are stacked upon one another to provide a sufficient number of conductive traces to match the number of transducer elements. As the number of transducer elements increases within the probe, the number of flexible circuits within the stack similarly increases which results in a stack of flexible circuits that becomes excessively thick and inflexible. The stack of flexible circuits is relatively inflexible and cannot easily bend around sharp corners. Instead, the thickness of the stack of flexible circuits limits the radius of curvature. The size and limited flexibility of the stack of conventional flexible circuits causes the stack of flexible circuits to take up a substantial amount of room within the housing of the probe which ultimately limits the ability to provide compact and a small probes that have a large number of individual transducer elements.

BRIEF DESCRIPTION OF THE INVENTION

In accordance with embodiments herein, an ultrasound probe is provided. The ultrasound probe comprises a two-dimensional (2D) transducer assembly having transducer elements arranged in rows and columns. The transducer elements have front and rear surfaces. The front surface is configured to transmit and receive ultrasound signals to and from an object of interest. A thin film flex circuit extends along the rear surface of the transducer assembly. The flex circuit has conductive traces arranged in layers and enclosed within a common dielectric layer. The dielectric layer has a homogeneous composition surrounding the layers of the conductive traces. The conductive traces are electrically interconnected to the corresponding transducer elements.

Optionally, the common dielectric layer may comprise a base dielectric coating and an intermediate dielectric coating. The intermediate dielectric coating may have a bottom surface that bonds directly to an upper surface of the base dielectric coating. The bottom surface of the intermediate dielectric coating may enclose a first layer of the conductive traces and may have an upper surface with a second layer of conductive traces formed thereon such that the intermediate dielectric coating provides the homogeneous composition between the adjacent first and second layers of conductive traces.

Optionally, the flex circuit may comprise multiple dielectric coatings directly bonded to one another along coating interfaces that form the homogeneous composition across the coating interface. The thin film flex circuit may comprise an additive composition of multiple dielectric coatings enclosing the conductive layers of the multiple traces. The transducer assembly may comprise at least 1000 transducer elements arranged in the rows and columns. The conductive traces within at least a first layer are spaced apart, in a transverse direction, by a trace separation spacing of between 10 and 25 µm, and may be configured to carry transmit signals having a peak voltage of 20V-100V. The conductive traces within adjacent first and second layers may be spaced apart, in a vertical direction, by a layer separation spacing of between 2 and 15 µm, and may be configured to carry transmit signals having a voltage of 20V-100V.

Optionally, the transducer elements may be arranged in a 16×16 matrix of rows and columns. A backing layer may be positioned with the flex circuit sandwiched between the backing layer and the rear surfaces of the transducer elements. The ultrasound probe may further comprise a probe body having a nose piece with an active imaging window therein. The nose piece may be configured to receive the transducer assembly with the outer surfaces of the transducer elements facing toward the active imaging window. The transducer assembly may be oriented to extend along an elevational direction with respect to the probe body. The transducer assembly may have elevational edges spaced apart from one another along the elevational direction. The flex circuit may be oriented to extend along the elevational direction.

Optionally, the flex circuit may have a connective segment positioned between the transducer assembly and a backing layer. The connective segment may interconnect the conductive traces of the flex circuit to corresponding transducer elements. The flex circuit may have leading and trailing segments extending beyond elevational edges of the transducer assembly and may wrap around and extend along the elevational sides of the backing layer away from an active imaging window.

In accordance with embodiments herein a method of manufacturing an ultrasound probe is provided. The method comprises providing a two-dimensional (2D) transducer assembly having transducer elements arranged in rows and columns. The transducer elements have an outer surface that is configured to transmit and receive ultrasound signals to and from an object of interest. The transducer elements have a rear surface. The method forms a thin film flex circuit. The flex circuit has multiple layers of conductive traces enclosed within a common dielectric layer utilizing an additive manufacturing process to provide a homogeneous composition between adjacent layers of the conductive traces. The ultrasound probe extends the flex circuit along the rear surface of the transducer assembly and interconnects the conductive traces of the flex circuit to the corresponding transducer elements.

Optionally, the forming operation may apply a base dielectric coating, build a first layer of conductive traces along an upper surface of the base dielectric coating, apply an intermediate dielectric coating to the upper surface of the base dielectric coating to at least partially enclose the first layer of conductive traces and may repeat the building and applying operations a select number of times. The method may further comprise after building the first layer of conductive traces, activating exposed regions of the upper surface of the base dielectric coating between the conductive traces to facilitate bonding with the intermediate dielectric coating.

Optionally, the building operation may comprise adding a seed layer to the base dielectric coating, creating a predetermined trace pattern in the seed layer, growing the first layer of conductive traces on the seed layer corresponding to the predetermined trace pattern, and removing photoresist regions within the inter-trace gaps to expose regions of the upper surface of the base dielectric layer between the conductive traces.

In accordance with embodiments herein, an ultrasound probe is provided comprising a probe body joined to a nose piece with an active imaging window therein. A two-dimensional (2D) transducer assembly is configured to fit within the nose piece proximate the active imaging window. The transducer assembly has transducer elements arranged in rows and columns. Control circuits manage operation of the transducer assembly. The ultrasound probe further comprises a backing layer. A thin film flex circuit has multiple layers of conductive traces enclosed within a common dielectric layer. The flex circuit includes an interconnect segment and at least one transition segment. The interconnect segment is held between the transducer assembly and the backing layer. The conductive traces, within the interconnect segment, are electrically interconnected to the corresponding transducer elements. The at least one transition segment extends beyond an elevational edge of the transducer assembly, wraps around a side of the backing layer and bends in a rearward direction away from the active imaging window toward the control circuits.

Optionally, the flex circuit may have at least 5 layers of conductive traces and may carry at least 1000 channels. The flex circuit may include a curved segment that wraps around the side of the backing layer with a radius of no more than 1.0 mm. The at least one transition segment may include a leading segment that includes a leading tail. The leading tail may extend along a lower surface of a pad to provide a lower portion that electrically connects to a first printed circuit board in the control circuits. The leading tail may wrap about an upper surface of the pad to provide an upper portion that electrically connects to a second printed circuit board in the control circuits. The nose piece may include a front face and side portions to form an interior cavity. The side portions may have interior walls spaced apart from the elevational edges of the transducer assembly by a distance of less than or equal to 1.5 mm.

DETAILED DESCRIPTION OF THE INVENTION

Figure 1A:
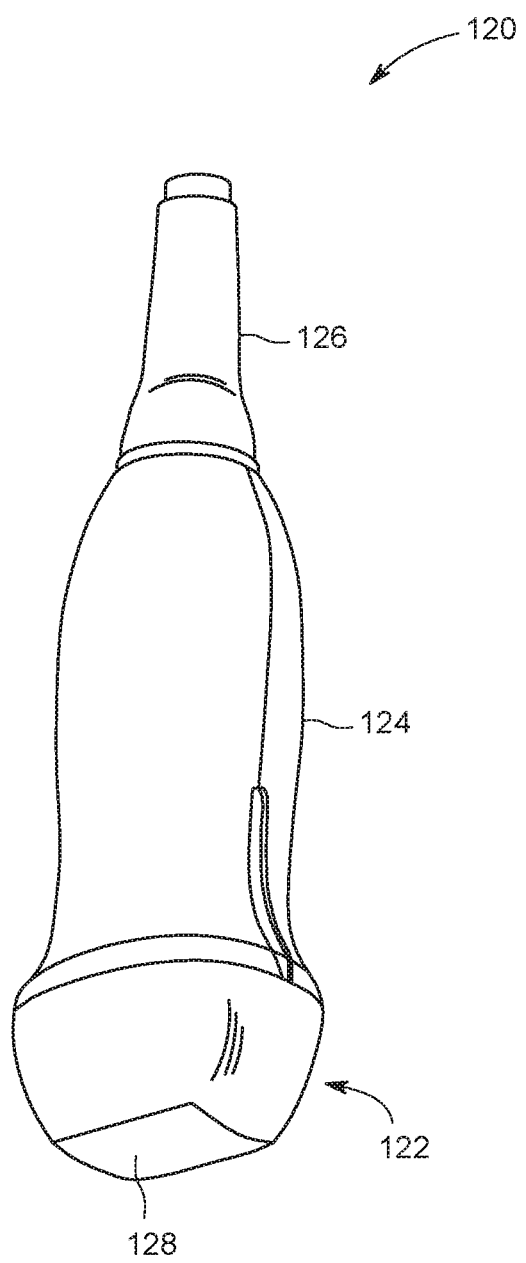
FIG. 1A illustrate an ultrasound probe formed in accordance with embodiments herein.

The following detailed description of certain embodiments will be better understood when read in conjunction with the appended drawings. To the extent that the FIGS. illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

The term "integral", as used throughout, refers to formation of a one piece thin-film flex circuit through an additive process.

The term "homogeneous composition", as used throughout, refers to the formation of multiple dielectric coatings directly bonded to one another through an additive manufacturing process without an addition of an intervening adhesive or other foreign material. It is recognized that the homogeneous composition may not be 100% homogeneous, but instead may exhibit slight variations in homogeneity within manufacturing tolerances. As one example, the interface between adjacent dielectric coatings may include residues of seed layers, residues of surface activation process. The term "homogeneous composition" does not include constructions of separately formed single layer flex circuits that are secured to one another in a stacked arrangement with intervening layers of adhesive. It is recognized that, while the dielectric coatings provide a homogeneous composition between two or more of the adjacent layers of conductive traces, separate and/or additional layers and materials may be provided around the upper and/or lower surfaces of the overall thin-film flex circuit. For example, one or more boundary layers may be added over the upper dielectric coating and/or over the lower dielectric coating, where the boundary layers exhibit desired characteristics, such as resistance to foreign materials, light, and the like.

Figure 1B:
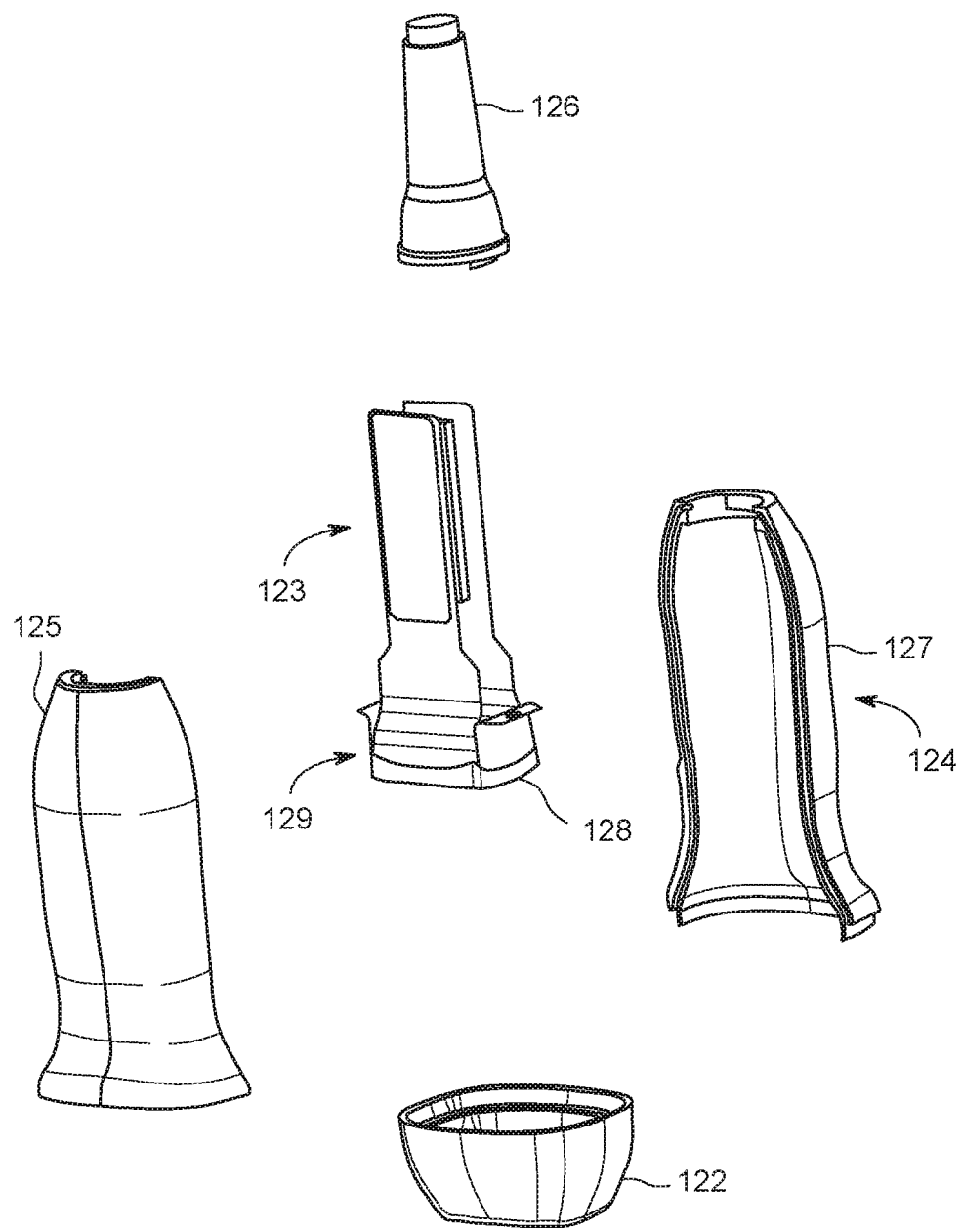
FIG. 1B illustrate the ultrasound probe of FIG. 1A in an exploded format in accordance with embodiments herein.

FIGS. 1A and 1B illustrate an ultrasound probe 120 formed in accordance with embodiments herein. As shown by FIG. 1B, ultrasound probe 120 comprises nose piece 122, main body 124, sleeve 126, lens 128, transducer array, and control circuits 123. The nose piece 122 extends at a forward end of probe 120 so as to at least partially enclose and support lens 128 and transducer array at an imaging window. The nose piece 122 comprises an outer polymeric casing wall which extends about lens 128. The body 124 comprises a tubular structure extending rearward from nose piece 122, although alternative shapes may be utilized. The body 124 supports the nose piece 122 while enclosing the transducer array and control circuits 123. The body 124 provides a structure by which a person may manually grip and manipulate the probe 120. In the example illustrated, body 124 is formed from two halves 125, 127 which are joined to one another about transducer array and control circuits 123. In other implementations, depending upon what portion of an anatomy for which ultrasound probe 120 is to be used, body 124 may be formed as a single integral unitary body or may have other sizes, shapes and configurations.

The sleeve 126 extends rearward from body 124 to guide and receive a cable. The sleeve 126 serves as a strain relief to relieve strain during flexing or bending of cable as a result of manipulation of ultrasound probe 120. In other implementations, sleeve 126 may be omitted. For example, in other implementations, ultrasound probe 120 may communicate with external display devices or external analysis devices in a wireless fashion using a wireless antenna contained within body 124. In such an implementation, power maybe supplied to probe 120 using a rechargeable battery. In such an implementation, sleeve 126 may be omitted. The lens 128 comprises an acoustic lens located at an end of the nose piece 122 to focus emitted sound waves. Optionally, the lens 128 may be omitted entirely. Although illustrated as being a generally linear cylinder, in other implementations, lens 128 may have other configurations, such as used in cardiac, abdominal, endocavity and other applications. During imaging by probe 120, the nose piece 122 of probe 120 may be placed upon or against the exterior of anatomy, or may be partially inserted into anatomy depending upon those portions of the anatomy which are to be imaged.

The control circuits 123 comprise one or more processors, ASICs and/or circuits configured to control operation of ultrasound probe 120. As one example, the control circuit 123 may be constructed, to integrate the electronics, as described in U.S. patent application Ser. No. 14/986,913, the complete subject matter of which is incorporated by reference in its entirety. For example, control circuits 123 may generate control signals controlling and directing emission of ultrasound waves by transducer array (e.g., transmit beamforming). Control circuits 123 may additionally facilitate the supply of power to a transducer array as well as conveying received ultrasound signals from the ultrasound probe 120 to an external computing device for analysis and display. In one implementation, the control circuit 123 comprises multiple printed circuit boards supporting one or more electronic components, such as sub-aperture beamforming circuits, electrical tuning components, communication components and other components for carrying out such functions. In other implementations, control circuits 123 may comprise an application-specific integrated circuit (ASIC) supported on a printed circuit board. In another implementation, control circuits 123 may comprise one or more processing units and an associated memory, wherein the one or more processing units follow instructions contained in the associated non-transitory computer-readable medium of the memory to perform or carry out such functions as the supply of power to transducer array, the control of the emission of ultrasound waves by transducer array and the transmission of signals representing sensed ultrasound reflections from the anatomy.

Figure 2:
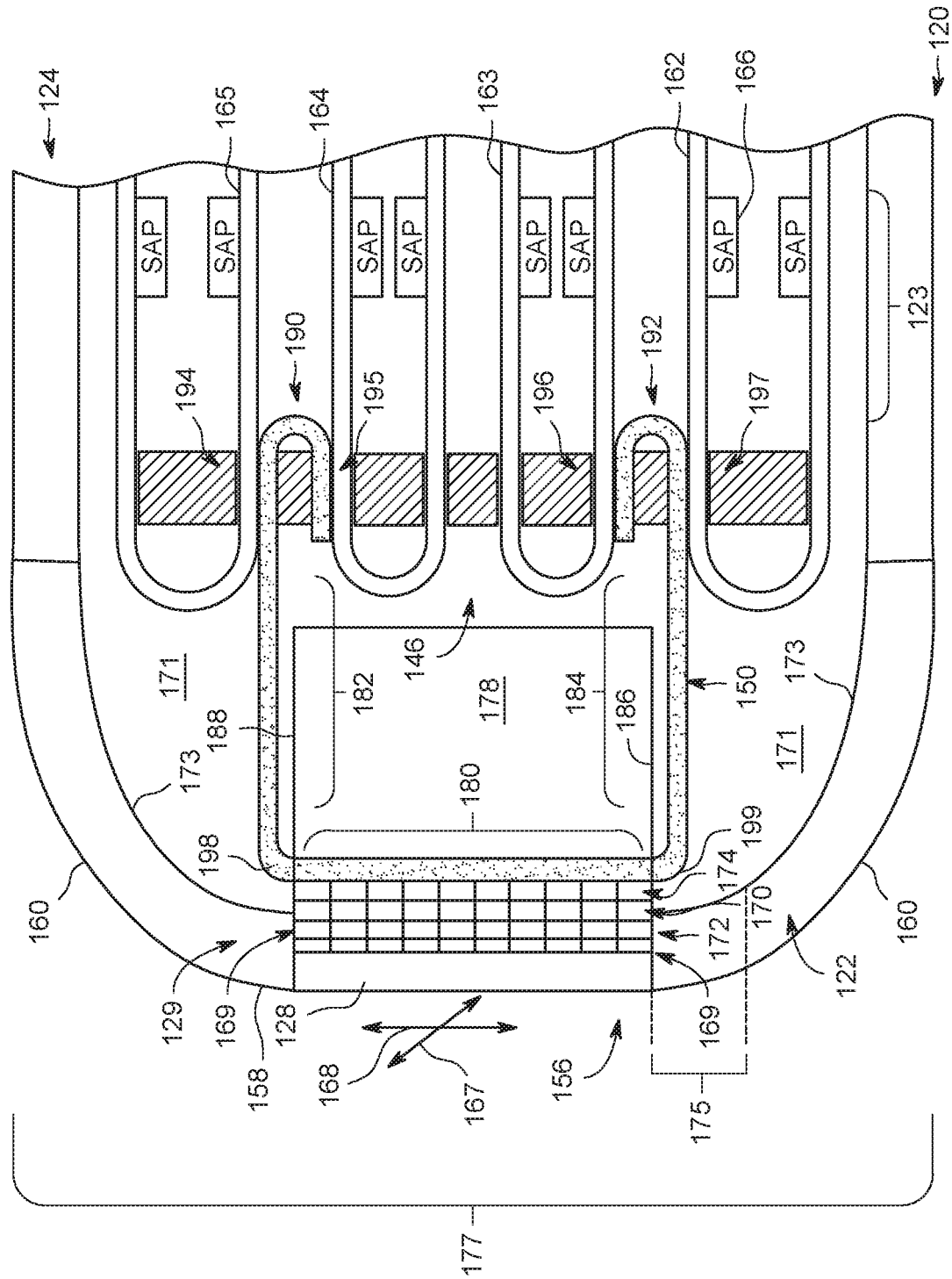
FIG. 2 illustrates a side sectional view of a header portion of the ultrasound probe of FIGS. 1A and 1B in accordance with embodiments herein.

FIG. 2 illustrates a side sectional view of a header portion of the ultrasound probe 120 of FIGS. 1A and 1B. The sectional view of FIG. 2 illustrates only a portion of the structures within the header portion of the ultrasound probe 120. The nose piece 122 has a front face 158 and lateral side portions 160 that curve to extend rearward, away from the front face 158. The front face 158 includes an active imaging window 156 that receives the lens 128. The front face 158 is formed integral with the lateral side portions 160 that extend rearward from the front face 158 back along the sides of the probe 120. The lateral side portions 160 are securely joined to the body 124. The nose piece 122 and body 124 receive various electronics including the transducer assembly 129, the control circuits 123 and mechanical mounting components 146. The control circuits 123 are electrically coupled to the transducer assembly 129 through a thin film flex circuit 150 that is formed in accordance with embodiments herein. The control circuits 123 include printed circuit boards 162-165 that are located within the body 124 of the probe 120. The printed circuit boards 162-165 have various electronic components mounted thereon, such as ASICs that are configured to perform sub aperture beamforming (referred to as SAP 166).

In the view of FIG. 2, the front face 158 and the lens 128 extend along an elevational direction 168 and an azimuthal direction 167, oriented orthogonal to one another. The transducer assembly 129 includes elevational edges 169 along opposite sides of a two-dimensional (2D) transducer array 170. The transducer assembly 129 also includes azimuthal edges (not shown). The transducer array 170 has transducer elements arranged in rows and columns. The transducer elements having front and rear surfaces, where the front surface is configured to transmit and receive ultrasound signals to and from an object of interest. The transducer array 170 includes one or more matching layers 172 provided over the front surfaces of the transducer elements (e.g., piezoelectric transducers) and a de-matching layer 174 provided over the rear surfaces of the transducer elements. The thin film flex circuit 150 extends along the rear surface of the transducer array 170. Optionally, the de-matching layer (DML) 174 may be omitted entirely. For example, an advantage of the thin film flex circuit 150 described herein is to provide a thin structure that is causes fewer acoustic perturbations (as compared to prior flex structures). Hence, the flex circuit 150 allows a non-DML structure.

The conductive traces of the flex circuit 150 are electrically interconnected with the rear surfaces of the transducer elements through contact pads (not visible in FIG. 2). The flex circuit 150 includes a connective segment 180 positioned adjacent the transducer assembly 129 with the contact pads positioned along the connective segment 180 to interconnect corresponding conductive traces to corresponding transducer elements. The connective segment 180 is sandwiched between the rear surfaces of the transducer elements (with one or more intervening layers), and more generally, the transducer assembly 129 and a backing layer 178. The flex circuit 150 includes at least one transition segment that extends beyond an elevational edge 169 of the transducer assembly 129 and wraps around a side 186, 188 of the backing layer 178 and bends in a rearward direction away from the active imaging window 156 toward the control circuits 123. For example, the transition segment may include one or both of a leading segment 182 and a trailing segment 184. One or both of the leading and trailing segments 182, 184 extend beyond the elevational edges 169 of the transducer assembly 129. The leading and trailing segments 182, 184 wrap around the sides 186, 188 of the backing layer 178 and bend in a rearward direction away from the active imaging window 156 toward the control circuits 123. The leading and trailing segments 182, 184 of the flex circuit 150 include leading and trailing tails 190, 192, respectively, that overlap and are electrically interconnected with the corresponding printed circuit boards 162-165. For example, the leading tail 190 abuts against and electrically interconnects with printed circuit boards 164, 165 in interface areas 194, 195. Similarly, the trailing tail 192 abuts against and electrically interconnects with the printed circuit boards 162, 163 at interface areas 196, 197. The flex circuit 150 and the printed circuit boards 162-165 provide a large number of individual communications channels (e.g., 1000 to 20000) between the control circuits 123 and corresponding individual transducer elements in the transducer array 170.

The leading and trailing segments 182, 184 join with the connective segment 180 at curved segments 198 and 199. As explained herein, in accordance with embodiments, the curved segments 198, 199 bend around a relatively small radius of curvature that enables the leading and trailing segments 182, 184 to conform closely to elevational sides 186, 188 of the backing layer 178. Enabling the leading and trailing segments 182, 184 to follow the elevational sides 186, 188, allows the interior cavity 171 and the overall the nose piece 122 be formed much smaller than in conventional ultrasound probes. For example, the interior walls 173 of the side portions 160 in an area proximate to the curved segments 198, 199, may be spaced close to the elevational sides 186, 188 of the backing layer 178 and to the elevational edges 169 of the transducer assembly 129. The spacing between the interior walls 173 and the elevational sides 186, 188 (and elevational edges 169 of the transducer assembly 129) is denoted as distance 175. By way of example, the distance 175 may be less than or equal to 1.5 mm. Maintaining the distance 175 relatively compact, leads to a smaller overall outer envelope 177 for the nose piece 122.

In accordance with embodiments herein, the ultrasound probe 120 is configured as an electronic four dimensional (4D) probe that comprises a set of transducer elements arranged in a 2D array (e.g., at least 1000). The 2D array may include at least a 16×16 matrix of rows and columns of transducer elements. As another example, the 2D array may include a matrix having a 64×128 element array, 60×100 element array, 40×60 element array and the like. The total number of transducer elements may be up to 4,000, or within a range from 1000 to 20000 elements, or more. The set of transducer elements are electrically joined to corresponding conductive traces within a single thin-film flex circuit 150. The conductive traces carrying signals to and from the corresponding transducer elements. The flex circuit 150 comprises a common dielectric material enclosing and arranging the conductive traces in multiple layers. The dielectric material includes multiple dielectric coatings formed through an additive technique. The dielectric layer has a homogeneous composition surrounding the layers of the conductive traces.

By way of example, the thin-film flex circuit may comprise 2 to 5 layers of conductive traces that are separated from one another by inter-trace gaps of 10-25 µm. As a further example, the conductive traces may be 2-10 µm thick (in the vertical direction). By way of example, adjacent layers of conductive traces may be separated from one another, vertically, by dielectric material having a vertical height of 2-15 µm, and more preferably 5-10 µm. By way of example, conductive via pads may be formed with a pad to pad spacing of 50-100 µm, and more specifically 50-75 µm.

Figure 3:
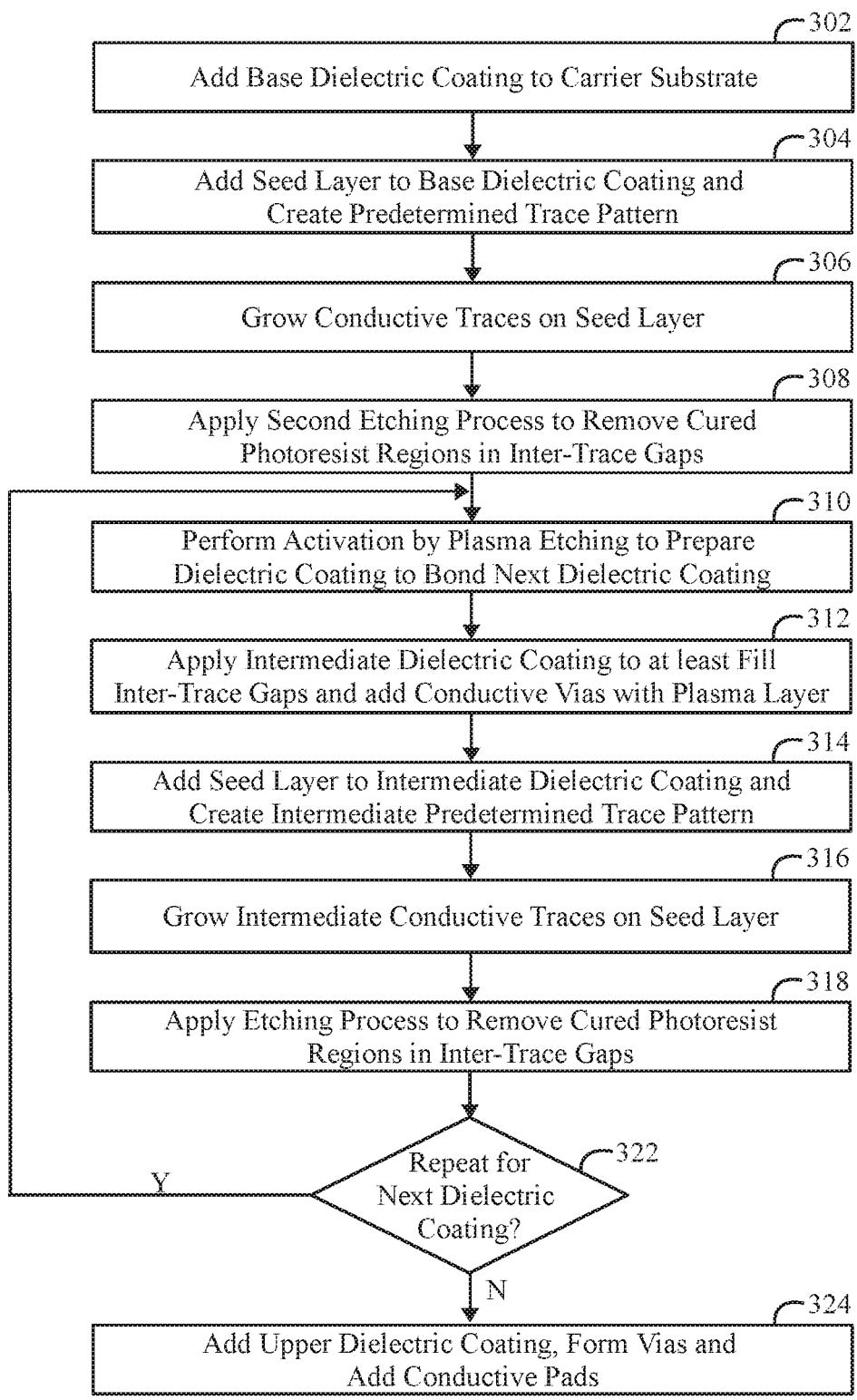
FIG. 3 illustrates an additive manufacturing process for forming thin-film flex circuit in accordance with embodiments herein.

FIG. 3 illustrates an additive manufacturing process for forming a thin-film flex circuit in accordance with embodiments herein. It is recognized that the process of FIG. 3 is one non-limiting example of an additive manufacturing process. Other additive manufacturing processes may be uses. Also, individual operations described in connection with FIG. 3 may be modified, replaced or omitted, while still resulting in an additive manufacturing process. Beginning at 302, a carrier substrate, such as a glass wafer, is positioned in a mold, and a base dielectric coating, such as polyimide material, is built onto the substrate. For example, a spin-coating technique may be utilized to add the base dielectric coating. During spin-coating, the base dielectric coating is provided in liquid form on the substrate, and the substrate is spun to produce centrifugal forces that cause the base dielectric coating to spread evenly circumferentially across the substrate. The base dielectric coating is then cured to form a solid layer.

At 304, a seed layer is added to the base dielectric coating and shaped into a predetermined trace pattern. For example, once the seed layer is added, a photoresist layer is applied to cover the seed layer. A mask, that includes the predetermined trace pattern, is placed over the photoresist layer to cover/block select portions from light and to expose other portions of the photoresist layer to light. Optionally, the mask may be omitted with certain types of processes, such as a Laser direct system (LDS). The predetermined trace pattern corresponds to a pattern in which it is desired to grow conductive traces on the seed and base dielectric coatings. The exposed portions of the photoresist layer are cured by the light, while the covered portions of the photoresist layer do not cure. Thereafter, the non-cured portions of the photoresist layer are then removed, such as through etching. The etching forms trenches in the photoresist layer along the non-cured areas. When the non-cured portions of the photoresist layer are removed, corresponding portions of the seed layer are exposed along the predetermined trace pattern defined by the mask. Optionally, additional or alternative processes may be utilized, such as processes that use negative photo-resist and positive photo-resist concepts.

At 306, conductive traces are grown on the exposed portions of the seed layer in the areas corresponding to the predetermined trace pattern defined by the mask. For example, the conductive traces may be grown utilizing a galvanic process, through which the conductor grows in the areas having the exposed seed layer in the trenches that follow the same pattern as the predetermined trace pattern of the seed layer. The seed layer facilitates bonding between the conductive material and the base dielectric coating. During the galvanic process, the conductive material builds up to form the conductive traces, while the regions retaining the cured photoresist do not experience build-up of the conductive material.

At 308, a second etching process is applied to remove the cured photoresist regions that are exposed and located between the conductive material that forms the conductive traces. The second etching process differs from the first etching process. The second etching process cleans and removes the cured photoresist regions and the underlying seed regions within the inter-trace gaps between adjacent conductive traces. The second etching process leaves the base dielectric coating exposed between the conductive traces. Optionally, the seed layer may be a metal and if so, another etching solution may be utilized to remove the seed layer. At 310, an activation operation is performed, such as through plasma etching, to prepare the base dielectric coating for bonding to a second/intermediate dielectric layer. The activation operation removes any residual photoresist, seed, or other material and electrically charges the corresponding region of the upper surface of the base dielectric coating. The activation operation also seeks to remove remainders of the photoresist.

At 312, the intermediate/second dielectric layer is applied (e.g., spin coated) to at least fill the gaps between the conductive traces. The second dielectric layer may also cover the exposed upper surface of the conductive traces. The second dielectric layer bonds to the base dielectric coating within the inter-trace gaps between adjacent conductive traces. Optionally, at 312, via holes may be drilled (e.g., with a laser) or etched (e.g., using photoresist based process) to form an opening in the dielectric layer to access the metal layer underneath.

At 314, a next seed layer is added to the second dielectric layer and shaped into a second predetermined trace pattern. For example, a photoresist layer is applied to cover the seed layer, and a mask, that includes the second predetermined trace pattern, is placed over the photoresist. Exposed portions of the photoresist layer are cured by the light, while the covered portions of the photoresist layer do not cure. Thereafter, the non-cured portions of the photoresist layer are then removed, such as through etching. When the non-cured portions of the photoresist layer are removed, corresponding portions of the second seed layer are exposed along the second predetermined trace pattern defined by the second mask. When the via holes are formed at 312, the seed layer that is applied may cover the entire surface, and thus also run into the via holes and contacts to the metal layer exposed at the bottom of the via hole.

At 316, intermediate conductive traces are grown on the exposed portions of the second seed layer in the areas corresponding to the second predetermined trace pattern and via designators. At 318, a next etching process is applied to remove the cured photoresist regions that are exposed and located between the conductive material that forms the intermediate conductive traces. The etching process leaves the intermediate dielectric layer exposed between the intermediate conductive traces.

At 322, a determination is made regarding whether a third dielectric layer is to be applied. If another layer is to be applied, the process returns to 310. Otherwise, the process continues to 324. The foregoing process is repeated to build a thin-film flex circuit through an additive process with a desired number of layers of conductive traces stacked upon one another within a common dielectric material.

At 324, a final/upper dielectric coating is applied, one or more conductive vias are formed through the upper dielectric coating and one or more conducive pads are formed on the upper dielectric coating.

Figure 4A:
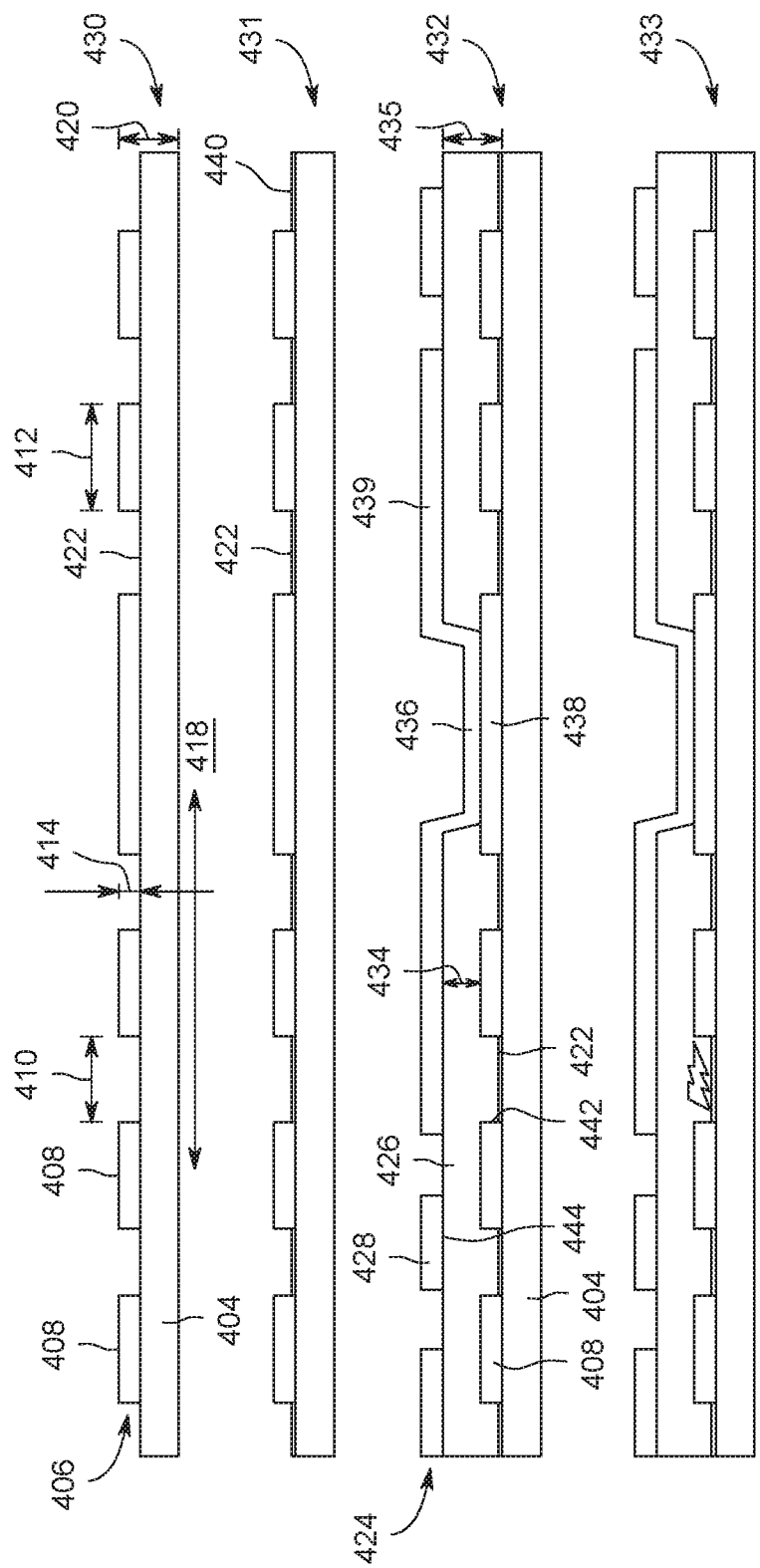
FIG. 4A illustrates a portion of a thin-film flex circuit at various stages of completion during the manufacturing process of FIG. 3 in accordance with embodiments herein.

FIG. 4A illustrates a portion of a thin-film flex circuit 150 at various stages of completion during the manufacturing process of FIG. 3. In the example of FIG. 4A, stages 430-433 are illustrated in connection with building two layers of conductive traces within a thin-film flex circuit. In FIG. 4A, at stage 430, a base dielectric coating 404 is provided with a first layer 406 of conductive traces 408 built onto an upper surface 422 of the base dielectric coating 404. The thin-film flex circuit 150 is illustrated in cross-section (e.g., in the transverse direction orthogonal to the elevational direction in FIG. 2) such that the base dielectric coating 404 is elongated to extend out of the FIG. The flex circuit 150 has a width extending in a transverse direction 418 (only a portion of which is illustrated) and a height or thickness extending in a vertical direction 420. Conductive traces 408 are shown in cross-section with a trace width 412 extending in the transverse direction 418 and a trace height/thickness 414 extending in the vertical direction 420. The conductive traces 408 are separated in the transverse direction 418 by a trace separation spacing 410. It is recognized that the stage 430 extends further in the transverse direction 418 and includes additional conductive traces 408.

In the process of FIG. 3, the upper surface 422 of the base dielectric coating 404 is activated to be prepared to bond to a next dielectric coating. In FIG. 4A, stage 431 illustrates the upper surface 422 in an activated state 440. Stage 432 illustrates the addition of a second dielectric coating 426 onto the upper surface 422 of the base dielectric coating 404. The second dielectric coating 426 may represent an intermediate coating when additional coatings are built there over. The second dielectric coating 426 is joined to the base dielectric coating 404 along the upper surface 422 such that the lower surface of the second dielectric coating 426 covers the conductive traces 408. The dielectric coatings 404 and 426 substantially enclose and electrically isolate the conductive traces 408. A next layer 424 of conductive traces 428 is formed on the dielectric coating 426 in accordance with the operations described above in connection with FIG. 3 (e.g., the operations at 310-322). The dielectric coating 426 is formed with a coating thickness 435 sufficient to space the adjacent layers 406 and 424 of conductive traces 408 and 428 apart from one another in the vertical direction by a layer separation spacing 434. The spacing 434 is measured between adjacent conductive traces 408 and 428 that are substantially vertically aligned with one another. An upper surface 444 of the second dielectric coating 426 includes one or more conductive vias 436 and conductive pads 439 configured to be utilized to provide an electrical connection between a corresponding conductive pad 438 in a lower layer and a conductive via in a next upper layer.

The dielectric coating 426 represents an intermediate coating and is formed integral with the base dielectric coating 404, wherein both dielectric coatings 426 and 404 have a uniform homogeneous structure and are bonded to one another along the activation layer 440. The intermediate dielectric coating 426 includes a bottom surface 442 that directly engages and surrounds the conductive traces 408 that are formed on the base dielectric coating 404. The intermediate dielectric coating 426 includes an upper surface 444, upon which the conductive traces 428 are formed. The trace separation spacing 410 and the layer separation spacing 434 have a predetermined (e.g., minimum) distance is that are defined to avoid an electrical discharge between adjacent traces in a common layer and/or within adjacent layers.

It is understood that the process described in connection with FIGS. 3 and 4A may be repeated to add more than two layers of conductive traces and more than two dielectric coatings. In accordance with at least one embodiment, a thin-film flex circuit may be constructed having five layers of conductive traces that are held within six layers of dielectric coatings.

Figure 4B:
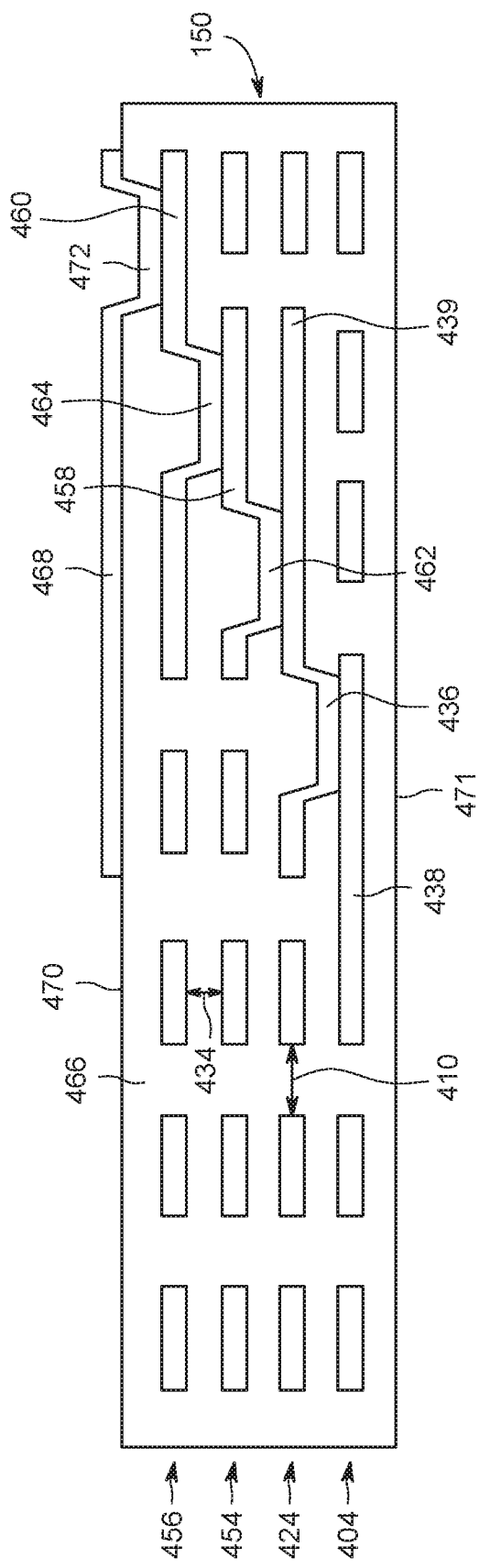
FIG. 4B illustrates a cross sectional view of the thin-film flex circuit of FIG. 2 upon completion of the additive manufacturing process described in connection with FIG. 3 and FIG. 4A in accordance with embodiments herein.

FIG. 4B illustrates a cross sectional view of the thin-film flex circuit 150 of FIG. 2 upon completion of the additive manufacturing process described in connection with FIGS. 3 and 4A. The thin-film flex circuit 150 includes the first and second layers 404, 424 of conductive traces, as described above, as well as third and fourth dielectric coatings 454 and 456 of conductive traces. Additional layers may be used. The layers 404, 424, 454 and 456 are enclosed within a dielectric layer 466, also referred to as a coating stack. The dielectric layer 466 is formed from multiple coatings of a homogeneous dielectric material, as explained above in connection with FIGS. 3 and 4A. Each of the layers 404, 424, 454 and 456 include at least one conductive pad 438, 439, 458 and 460, respectively. An upper contact pad 468 is formed on the upper surface 470 of the dielectric layer 466. The upper contact pad 468 is joined, through a via 472 to the configuration of vertically arranged vias 436, 462, 464 and 472 in order to electrically connect the upper contact pad 468 with one or more conductive traces within the dielectric layer 466. The vias 436, 462, 464 and 472 are staggered in the vertical direction (along the thickness of the flex circuit 150). The construction of the flex circuit 150 is void of adhesive layers.

In the example of FIG. 4B, at least one conductive trace in the first layer 404 is interconnected through the contact pad 438 and the series of vias with the upper contact pad 468. Multiple combinations of conductive pads and vias may be provided within the flex circuit 150 to provide a point of electrical connection for each conductive trace on the upper surface 470 or lower surface 471 of the flex circuit 150.

In accordance with embodiments herein, a thin-film flex circuit 150 is formed with a plurality of conductive traces stacked in multiple layers 404, 424, 454, 456 within a common homogeneous dielectric material. Embodiments herein provide the plurality of conductive traces in a compact manner with trace separation spacing 410 and layer separation spacing 434. For example, horizontally adjacent conductive traces (traces aligned in a common lateral plane) within at least a first layer are spaced apart, in a transverse direction, by a trace separation spacing of between 10 and 25 μm, and are configured to carry transmit signals having a peak voltage of 20V-100V. For example, the conductive traces within adjacent first and second layers are spaced apart, in a vertical direction, by a layer separation spacing of between 2 and 15 μm, and are configured to carry transmit signals having a voltage of 20V-100V. The trace width 412 extending in the azimuthal/transverse direction 418 may be 10-25 μm and the trace height/thickness 414 extending in the vertical direction 420 may be 2-15 μm. From the foregoing dimensional ranges, a flex circuit 150, with 5 conductive layers, may have an overall thickness/height between the upper and lower surfaces 470, 471 of between 40 μm and 150 μm, and more specifically between 45 μm and 135 μm.

In accordance with aspects herein, the additive manufacturing process provides the flex circuit 150 with high trace resolution and high flexibility as compared to conventional flex circuits that are built utilizing subtractive manufacturing processes. The flex circuit 150 provides a high density of integrated interconnects which improves ergonomics and thermal design, as well as reducing probe weight and size. The increased flexibility of the flex circuit 150 allows the nose piece 122 to be formed with a relatively small envelope, as compared to the nose piece of conventional electronic 4D ultrasound probes. In accordance with aspects herein, the additive manufacturing process yields a cost effective manufacturing process that affords a high level of component integration as well as a simplified interconnect lamination process. By simplifying the lamination process, the manufacturing yield is increased.

In accordance with embodiments herein, the thin-film flex circuit is formed with multiple dielectric coatings bonded directly to one another without any intervening layers of another material. Successive dielectric coatings are joined along a coating to coating interface in which the dielectric material from adjacent coatings directly links to and intermingles with one another. The successive dielectric coatings are joined in an adhesive-less manner through an additive process. In accordance with embodiments herein, the thin-film flex circuit is constructed using an additive manufacturing process for building a high density flex interconnect for ultrasound transducers. The additive process affords higher integration, less components, and higher density of interconnect as compared to conventional flex circuits. By way of example, the thin film flex circuit may have at least 5 layers of conductive traces that carry at least 1000 channels that support a peak voltage of 20-100V within an overall vertical thickness of 50-400 μm.

Figure 4C:
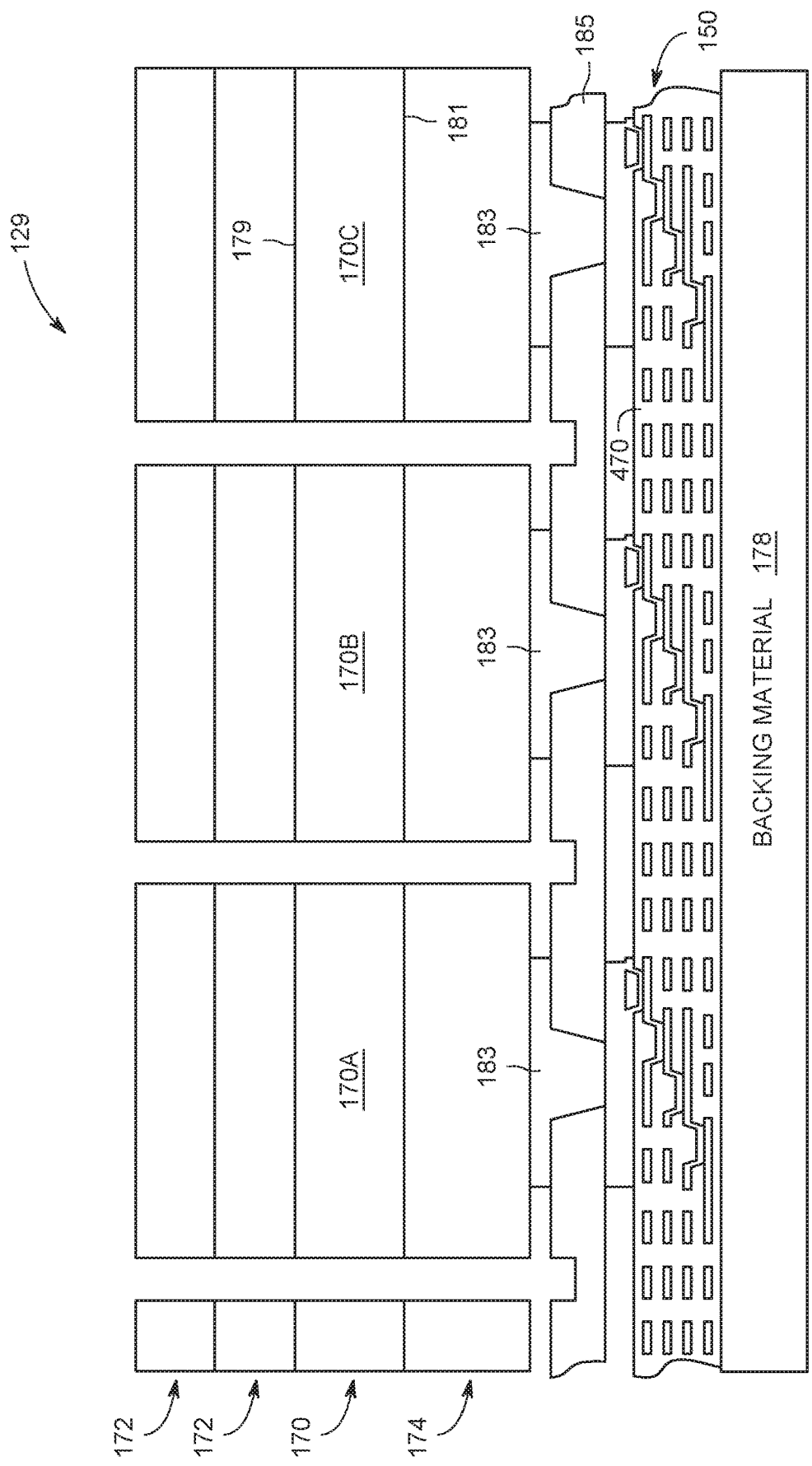
FIG. 4C illustrates a side sectional view of a portion of the header section of the ultrasound probe of FIGS. 1A, 1B, and 2 in accordance with embodiments herein.

FIG. 4C illustrates a side sectional view of a portion of the header section of the ultrasound probe of FIGS. 1 and 2. In FIG. 4C, the transducer assembly 129, flex circuit 150 and backing layer 178 are illustrated in more detail. The transducer assembly 129 includes first and second matching layers 172 that are stacked upon one another. The matching layers 172 are stacked on the transducer array 170 that has transducer elements 170A-170C arranged in a two-dimensional matrix of rows and columns (only one row or column is illustrated in FIG. 4C in the side sectional view). The transducer elements 170A-170C have front and rear surfaces 179, 181, where the front surface 179 is configured to transmit and receive ultrasound signals to and from an object of interest. The one or more matching layers 172 are provided over the front surfaces 179 of the transducer elements 170A-170C (e.g., piezoelectric transducers). A de-matching layer 174 may be provided over the rear surfaces 181 of the transducer elements 170A-170C.

The conductive traces of the flex circuit 150 are electrically interconnected with the rear surfaces 181 of the transducer elements 170A-170C through contact pads 183 that are joined with one another through an interposer flex 185. An adhesive would fill the voids between the surface pads of the components. Contact may be made through either direct metal to metal contact or by using an adhesive that includes conductive particles.

The contact pads 183 are joined with corresponding contact pads on the upper surface 470 of the flex circuit 150 and are subsequently interconnected with one or more corresponding conductive traces through a corresponding network of vias and interior contact pads within the thin film flex circuit 150 form a unique and separate communications channel to convey signals to and from each individual transducer element 170A-170C. While not illustrated, a similar arrangement of contact pads is provided at the interfaces 194-197 (FIG. 2) between the leading and trailing tails 190, 192 of the flex circuit 150 and the printed circuit boards 162-165.

Figure 5A:
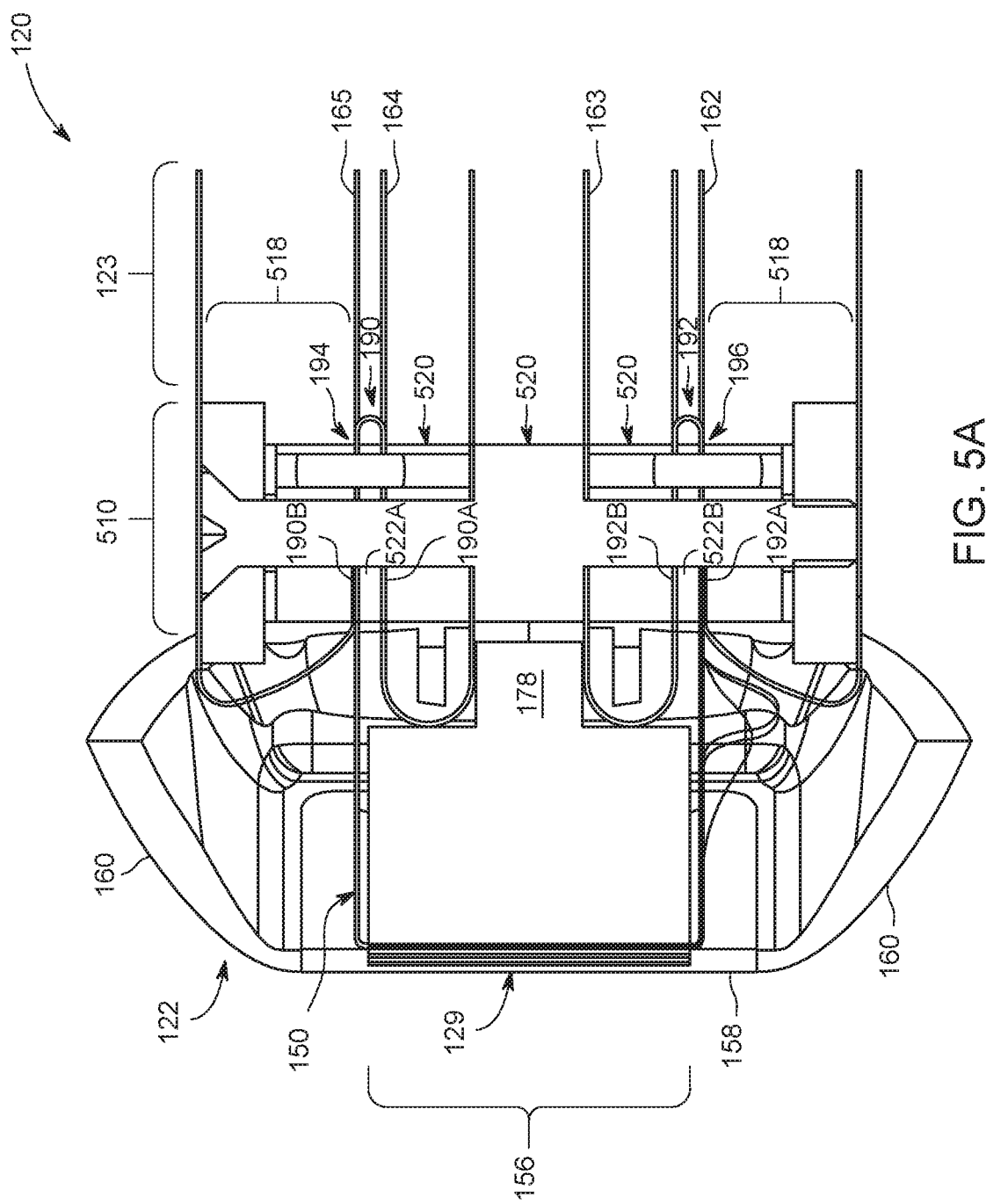
FIG. 5A illustrates a side sectional view of a portion of the ultrasound probe formed in accordance with an embodiment herein in accordance with embodiments herein.

FIG. 5A illustrates a side sectional view of a portion of the ultrasound probe 120 formed in accordance with an embodiment herein. FIG. 5A illustrates the nose piece 122 with the main body 124 (FIG. 1A) removed. The nose piece 122 has the active imaging window 156 provided within the front face 158. The front face 158 is formed integral with lateral side portions 160 that extend rearward from the front face 158. The main body 124 and 122 receive various electronics including a transducer assembly 129, a backing layer control circuits 123 and a mechanical mounting assembly 510.

The mechanical mounting assembly 510 holds the leading and trailing tails 190, 192 in a desired electrically connection with the PCBs 162-165. The PCBs 162-165 wrap about mounting elements within the mounting assembly 510. The mounting assembly 510 includes clamps 518 located on opposite ends of the stack of mounting elements. For example, the clamps 518 may include a spring steel outer portion and an aluminum interior portion where the interior aluminum portions are configured to abut against surfaces of corresponding PCBs 162-165. Mechanical spacers 520 are provided to separate adjacent parallel layers of the PCBs by predetermined distances to afford room for electronic components to be mounted to the surfaces of the PCBs 162-165. Rubber pads 522A, 522B are provided at the interface areas 194 and 196. The leading and trailing tails 190, 192 of the circuit board 150 wrap about the rubber pads 522A and 522B, where the leading and trailing tails 190, 192 are then joined to corresponding PCBs. The leading and trailing tails 190, 192 are bent round a relative small curvature having a diameter that corresponds to the thickness of the rubber pads 522A, B, to provide a relatively close spacing between adjacent segments of the PCBs 162 and 163, and adjacent segments of the PCBs 164 and 165. For example, the leading tail 190 extends along a lower surface of the rubber pad 522A to provide a lower portion 190A that electrically connects to PCB 164. The leading tail 190 wraps about an upper surface of the rubber pad 522A to provide an upper portion 190B that electrically connects to PCB 165. The lower and upper portions 190A, B of the leading tail 190 are located along a common side of the leading tail 190. The lower and upper portions 190A, B include a configuration of vias and contact pads (similar to the arrangements shown in FIGS. 4A-4B to provide electrical connections between conductive traces in the flex circuit 150 and the PCBs 164, 165. The trailing tail 192 extends along a lower surface of the rubber pad 522B to provide a lower portion 192A that electrically connects to PCB 162. The trailing tail 192 wraps about an upper surface of the rubber pad 522B to provide an upper portion 192B that electrically connects to PCB 163. The lower and upper portions 192A, B of the trailing tail 192 are located along a common side of the trailing tail 192. The lower and upper portions 192A, B include a configuration of vias and contact pads (similar to the arrangements shown in FIGS. 4A-4B to provide electrical connections between conductive traces in the flex circuit 150 and the PCBs 162, 163. In the present embodiment, the single flex circuit 150 supports separate channels between each of the transducer elements in the transducer assembly 129 and a corresponding trace on one of the four PCBs 162-165.

Figure 5B:
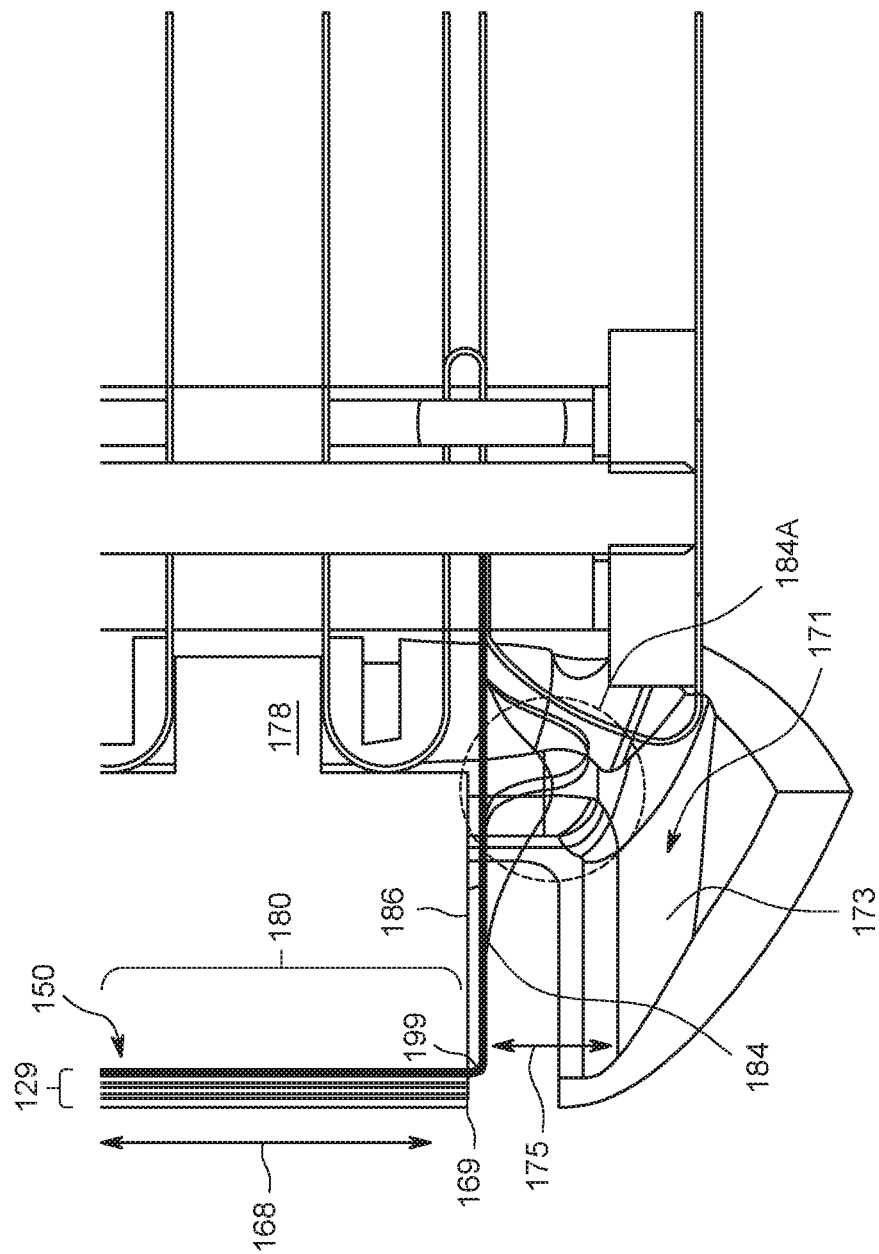
FIG. 5B illustrates an enlarged side sectional view of a portion of the ultrasound probe of FIG. 5A to illustrate the structures within the elevational regions of the nose piece in accordance with embodiments herein.

FIG. 5B illustrates an enlarged side sectional view of a portion of the ultrasound probe 120 of FIG. 5A to illustrate the structures within the elevational regions of the nose piece 122. In FIG. 5B, only a portion of the nose piece 122 is illustrated. Although, it is recognized that the illustrated portion of the nose piece 122 has a corresponding mirrored structure. As shown in FIG. 5B, the transducer assembly 129 extends in the elevation direction 168 and includes opposed elevational edges 169 (one of which is illustrated). The connective segment 180 of the flex circuit 150 is positioned between the transducer assembly 129 and the backing layer 178, while the trailing segment 184 extends beyond the elevational edges 169. The trailing segment 184 bends at curved segment 199 to wrap around and extend along the elevational side 186 of the backing layer 178.

FIG. 5B also illustrates in more detail the interior cavity 171 within the nose piece 122. The side portions 160 include interior surfaces 173 that are spaced in the elevational direction 168 from the sides 186 of the backing layer 178 by a gap 175. The curved segment 199 bends around a relatively small radius of curvature that enables the trailing segment 184 to conform closely to elevational side 186 of the backing layer 178, thereby enabling the interior cavity 171 within the nose piece 122 be relatively small. For example, the spacing between the interior wall 173 and the elevational side 186 is denoted as distance 175. Maintaining the distance 175 relatively compact, leads to a smaller overall outer envelope 177 for the nose piece 122.

In accordance with embodiments herein, the flex circuit 150 is able to be bent, at the curved segment 199, at a relatively sharp angle around a corner of the backing layer 178. For example, the curved segment 199 may have a radius of no more than 1 mm, for a thin film flex circuit having at least 5 layers of conductive traces and carrying at least 1000 channels. As a further example, the radius of the curved segment 199 may be approximately 1.5 mm, for a thin film flex circuit having at least 5 layers of conductive traces and carrying at least 1000 channels.

Optionally, FIG. 5B illustrates the trailing segment 184 separated into a plurality of strips in area 184A. The leading and trailing segments 182, 184 may be cut along the elevational direction (e.g., along a length of the flex circuit 150) into parallel strips in connection with certain types of shapes for the transducer assembly 129. For example, the transducer assembly 129, backing layer 178 and connective segment 180 of the flex circuit 150 may be shaped in a convex shape, relative to the active imaging window. In utilizing a convex shape, the transducer assembly 129, backing layer 178 and connective segment 180 are curved in the elevational and azimuthal directions similar to a circular or elliptical sphere. The circular or elliptical sphere creates an arc shaped interface (in the azimuthal direction) along the curved segment 199 (e.g., arc shaped into the sheet of FIG. 5B). The shaped interface creates separate amounts of slack in the strips of the flex circuit 150 which are illustrated in the area 184A. For example, strips of the flex circuit 150 near azimuthal edges of the transducer assembly 129 and backing layer 178 will have more slack than strips of the flex circuit 150 near an elevational center of the transducer assembly 129.

CLOSING STATEMENTS

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. An ultrasound probe, comprising:
a two-dimensional (2D) transducer assembly having transducer elements arranged in rows and columns, the transducer elements having front and rear surfaces, the front surface configured to transmit and receive ultrasound signals to and from an object of interest; and
a thin film flex circuit extending along the rear surface of the transducer assembly, the flex circuit having conductive traces arranged in layers and enclosed within a common dielectric layer, the dielectric layer having a homogeneous composition surrounding the layers of the conductive traces, the conductive traces electrically interconnected to the corresponding transducer elements.

2. The ultrasound probe of claim 1, wherein the common dielectric layer comprises a base dielectric coating and an intermediate dielectric coating, the intermediate dielectric coating having a bottom surface that bonds directly to an upper surface of the base dielectric coating, the bottom surface of the intermediate dielectric coating enclosing a first layer of the conductive traces and having an upper surface with a second layer of conductive traces formed thereon, the intermediate dielectric coating providing the homogeneous composition between the adjacent first and second layers of conductive traces.

3. The ultrasound probe of claim 1, wherein the flex circuit comprises multiple dielectric coatings directly bonded to one another along coating interfaces that form the homogeneous composition across the coating interface.

4. The ultrasound probe of claim 1, wherein the thin film flex circuit comprises an additive composition of multiple dielectric coatings enclosing the conductive layers of the multiple traces.

5. The ultrasound probe of claim 1, wherein the transducer assembly comprises at least 1000 transducer elements arranged in the rows and columns.

6. The ultrasound probe of claim 1, wherein the conductive traces within at least a first layer are spaced apart, in a transverse direction, by a trace separation spacing of between 10 and 25 µm, and are configured to carry transmit signals having a peak voltage of 20V-100V.

7. The ultrasound probe of claim 1, wherein the conductive traces within adjacent first and second layers are spaced apart, in a vertical direction, by a layer separation spacing of between 2 and 15 µm, and are configured to carry transmit signals having a voltage of 20V-100V.

8. The ultrasound probe of claim 1, wherein the transducer elements are arranged in a 16×16 matrix of rows and columns.

9. The ultrasound probe of claim 1, further comprising a backing layer that is positioned with the flex circuit sandwiched between the backing layer and the rear surfaces of the transducer elements.

10. The ultrasound probe of claim 1, further comprising a probe body having a nose piece with an active imaging window therein, the nose piece configured to receive the transducer assembly with the outer surfaces of the transducer elements facing toward the active imaging window.

11. The ultrasound probe of claim 1, wherein the transducer assembly is oriented to extend along an elevational direction with respect to the probe body, the transducer assembly having elevational edges spaced apart from one another along the elevational direction, the flex circuit is oriented to extend along the elevational direction.

12. The ultrasound probe of claim 1, wherein the flex circuit has a connective segment positioned between the transducer assembly and a backing layer, the connective segment to interconnect the conductive traces of the flex circuit to corresponding transducer elements, the flex circuit having leading and trailing segments extending beyond elevational edges of the transducer assembly and wrapping around and extending along the elevational sides of the backing layer away from an active imaging window.

13. A method of manufacturing an ultrasound probe, comprising:
 providing a two-dimensional (2D) transducer assembly having transducer elements arranged in rows and columns, the transducer elements having an outer surface that is configured to transmit and receive ultrasound signals to and from an object of interest, the transducer elements having a rear surface;
 forming a thin film flex circuit the flex circuit having multiple layers of conductive traces enclosed within a common dielectric layer utilizing an additive manufacturing process to provide a homogeneous composition between adjacent layers of the conductive traces; and
 extending the flex circuit along the rear surface of the transducer assembly; and
 interconnecting the conductive traces of the flex circuit to the corresponding transducer elements.

14. The method of claim 13, wherein the forming operation comprises:
 applying a base dielectric coating;
 building a first layer of conductive traces along an upper surface of the base dielectric coating;
 applying an intermediate dielectric coating to the upper surface of the base dielectric coating to at least partially enclose the first layer of conductive traces; and
 repeating the building and applying operations a select number of times.

15. The method of claim 14, further comprising, after building the first layer of conductive traces, activating exposed regions of the upper surface of the base dielectric coating between the conductive traces to facilitate bonding with the intermediate dielectric coating.

16. The method of claim 14, wherein the building operation comprises adding a seed layer to the base dielectric coating, creating a predetermined trace pattern in the seed layer, growing the first layer of conductive traces on the seed layer corresponding to the predetermined trace pattern, and removing photoresist regions within the inter-trace gaps to expose regions of the upper surface of the base dielectric layer between the conductive traces.

17. An ultrasound probe, comprising:
 a probe body joined to a nose piece with an active imaging window therein;
 a two-dimensional (2D) transducer assembly configured to fit within the nose piece proximate the active imaging window, the transducer assembly having transducer elements arranged in rows and columns;
 control circuits to manage operation of the transducer assembly;
 a backing layer;
 a thin film flex circuit having multiple layers of conductive traces enclosed within a common dielectric layer, the flex circuit including an interconnect segment and at least one transition segment, the interconnect segment held between the transducer assembly and the backing layer, the conductive traces, within the interconnect segment, electrically interconnected to the corresponding transducer elements;
 the at least one transition segment extending beyond an elevational edge of the transducer assembly, wrapping around a side of the backing layer and bending in a rearward direction away from the active imaging window toward the control circuits.

18. The ultrasound probe of claim 17, wherein the flex circuit has at least 5 layers of conductive traces and carries at least 1000 channels, the flex circuit including a curved segment that wraps around the side of the backing layer with a radius of no more than 1.0 mm.

19. The ultrasound probe of claim 17, wherein the at least one transition segment includes a leading segment that includes a leading tail, the leading tail extending along a lower surface of a pad to provide a lower portion that electrically connects to a first printed circuit board in the control circuits, the leading tail wrapping about an upper surface of the pad to provide an upper portion that electrically connects to a second printed circuit board in the control circuits.

20. The ultrasound probe of claim 17, wherein the nose piece includes a front face and side portions to form an interior cavity, the side portions having interior walls spaced apart from the elevational edges of the transducer assembly by a distance of less than or equal to 1.5 mm.

* * * * *